United States Patent [19]

Child et al.

[11] Patent Number: 5,191,150

[45] Date of Patent: Mar. 2, 1993

[54] METHOD FOR SEPARATING CONJUNCT POLYMERIC BYPRODUCTS FROM MIXTURE CONTAINING HYDROFLUORIC ACID AND A SULFONE

[75] Inventors: Jonathan E. Child; Tomas R. Melli, both of Sewell, N.J.; Sergei Yurchak, Media, Pa.

[73] Assignee: Mobil Oil Corporation, Fairfax, Va.

[21] Appl. No.: 833,684

[22] Filed: Feb. 11, 1992

[51] Int. Cl.$^5$ .......................... C07C 7/00; C07C 2/58; C07C 2/00; B01J 20/34

[52] U.S. Cl. ..................... 585/809; 585/802; 585/867; 585/709; 585/724; 585/730; 585/500; 585/502; 585/520; 502/31

[58] Field of Search .............. 585/809, 802, 867, 709, 585/724, 730, 500, 502, 520; 502/31

[56] References Cited

U.S. PATENT DOCUMENTS

| | | | |
|---|---|---|---|
| 2,615,908 | 10/1952 | McCaulay et al. | 260/438 |
| 3,531,546 | 9/1970 | Hervert et al. | 260/683.51 |
| 3,778,489 | 12/1973 | Parker et al. | 260/683.43 |
| 3,795,712 | 3/1974 | Torck et al. | 260/671 |
| 3,856,764 | 12/1974 | Throckmorton et al. | 260/82.1 |
| 4,025,577 | 5/1977 | Siskin et al. | 260/683.51 |
| 4,094,924 | 6/1978 | Siskin et al. | 260/683.51 |
| 4,938,935 | 7/1990 | Audeh et al. | 423/240 |
| 4,938,936 | 7/1990 | Yan | 423/240 |
| 4,985,220 | 1/1991 | Audeh et al. | 423/240 |

OTHER PUBLICATIONS

Handbook of Petroleum Engineering–Phillips HF Alkylation Process for Alkylation of $C_3$, $C_4$, and $C_5$ Olefins (1986) pp. 1-23 to 1-28.

Primary Examiner—Anthony McFarlane
Assistant Examiner—Nhat Phan
Attorney, Agent, or Firm—Alexander J. McKillop; Dennis P. Santini; Robert B. Furr, Jr.

[57] ABSTRACT

A method for separating conjunct polymers and sulfolane from a mixture containing conjunct polymers, sulfolane, and hydrofluoric acid is disclosed, which method comprises the sequential steps of separating hydrofluoric acid from said mixture to provide an intermediate stream containing less than about 30 percent hydrofluoric acid by weight and gravitationally separating said intermediate stream into a sulfolane-enriched stream and a conjunct polymer-enriched stream.

8 Claims, No Drawings

METHOD FOR SEPARATING CONJUNCT POLYMERIC BYPRODUCTS FROM MIXTURE CONTAINING HYDROFLUORIC ACID AND A SULFONE

FIELD OF THE INVENTION the present invention relates to the art of catalytic alkylation. More specifically, the invention relates to a liquid alkylation catalyst and an isoparaffin:olefin alkylation process. Particularly, the invention provides a liquid alkylation catalyst composition which avoids many of the safety and environmental concerns associated with concentrated hydrofluoric acid.

BACKGROUND OF THE INVENTION

Alkylation is a reaction in which an alkyl group is added to an organic molecule. Thus an isoparaffin can be reacted with an olefin to provide an isoparaffin of higher molecular weight. Industrially, the concept depends on the reaction of a $C_2$ to $C_5$ olefin with isobutane in the presence of an acidic catalyst producing a so-called alkylate. This alkylate is a valuable blending component in the manufacture of gasolines due not only to its high octane rating but also to its sensitivity to octane-enhancing additives.

Industrial alkylation processes have historically used concentrated hydrofluoric or sulfuric acid catalysts under relatively low temperature conditions. Acid strength is preferably maintained at 88 to 94 weight percent by the continuous addition of fresh acid and the continuous withdrawal of spent acid. As used herein, the term "concentrated hydrofluoric acid" refers to an essentially anyhydrous liquid containing at least about 85 weight percent HF.

Hydrofluoric and sulfuric acid alkylation processes share inherent drawbacks including environmental and safety concerns, acid consumption, and sludge disposal. For a general discussion of sulfuric acid alkylation, see the series of three articles by L. F. Albright et al., "Alkylation of Isobutane with $C_4$ Olefins", 27 *Ind. Enc. Chem. Res.*, 381–397, (1988). For a survey of hydrofluoric acid catalyzed alkylation, see 1 *Handbook of Petroleum Refining Processes* 23–28 (R. A. Meyers, ed., 1986).

Hydrogen fluoride, or hydrofluoric acid (HF) is highly toxic and corrosive. However, it is used as a catalyst in isomerization, condensation, polymerization and hydrolysis reactions. The petroleum industry used anhydrous hydrogen fluoride primarily as a liquid catalyst for alkylation of olefinic hydrocarbons to produce alkylate for increasing the octane number of gasoline. Year of experience in its manufacture and use have shown that HF can be handled safely, provided the hazards are recognized and precautions taken. Though many safety precautions are taken to prevent leaks, massive or catastrophic leaks are feared primarily because the anhydrous acid will fume on escape creating a vapor cloud that can be spread for some distance. Previous workers in this field approached this problem from the standpoint of containing or neutralizing the HF cloud after its release.

U.S. Pat. Nos. 4,938,935 and 4,985,220 to Audeh and Greco, as well as U.S. Pat. No. 4,938,936 to Yan teach various methods for containing and/or neutralizing H acid clouds following accidental releases.

But it would be particularly desirable to provide an additive which decreases the cloud forming tendency of HF without compromising its activity as an isoparaffin-:olefin alkylation catalyst. Solvents an complexing agents for hydrofluoric acid have, in the past, been disclosed for various purposes as noted in the following references.

U.S. Pat. No. 2,615,908 to McCaulay teaches thioether-HF-copper complex compounds and a method for preparing the same. Potential uses for the thioether-HF-copper composition compounds are listed from column 6, line 55 through column 8 at line 3. The method is said to be useful for purifying HF-containing vent gases from an industrial HF alkylation plant. See column 7, lines 10–24.

U.S. Pat. No. 3,531,546 to Hervert discloses a HF-$CO_2$ catalyst composition which is said to be useful for alkylation as well as olefin isomerization.

U.S. Pat. No. 3,795,712 to Torck et al. relates to acid catalysts comprising a Lewis acid, a Bronsted acid, and a sulfone of the formula R-$SO_2$-R', where R and R' are each separately a monovalent radical containing from 1 to 8 carbon atoms or form together a divalent radical having from 3 to 12 carbon atoms.

U.S. Pat. No. 3,856,764 to Throckmorton et al. teaches an olefin polymerization catalyst comprising (1) at least one organoaluminum compound, (2) at least one nickel compound selected from the class consisting of nickel salts of carboxylic acids, organic complex compounds of nickel, or nickel tetracarbonyl and (3) at least one hydrogen fluoride complex prepared by complexing hydrogen fluoride with a member of the class consisting of ketones, ethers, esters, alcohols, nitriles, and water.

U.S. Pat. No. 4,025,577 and 4,099,924 to Siskin et al. report the use of alkylation catalyst compositions containing HF, a metal halide, and sulfolane. U.S. Patent to Olah relates to an additive formulation which reduces the fuming tendency of HF.

Promoters such as alcohols, thiols, water, ethers, thioethers, sulfonic acids, and carboxylic acids are disclosed in combination with strong Bronsted acids such as HF, fluorosulfonic and trihalomethanesulfonic acids in U.S. Pat. 3,778,489 to Parker et al. The promoters are said to modify the activity of the strong Bronsted acids for alkylation.

The preceding references demonstrate the desirability of a liquid Bronsted acid catalyst (such as HF) for isoparaffin:olefin alkylation, as well the utility of liquid Bronsted acids in combination with metal halides, particularly metal fluorides.

In U.S. application Ser. No. 07/719,879, filed Jun. 21, 1991, an isoparaffin-olefin alkylation process is disclosed which uses an HF/sulfolane catalyst containing relatively high concentrations of sulfolane, and is incorporated by reference for the details of isoparaffin-olefin alkylation with a sulfolane-enriched HF catalyst.

SUMMARY OF THE INVENTION

The present invention provides a method for separating conjunct polymers and sulfolane from a mixture containing conjunct polymers, sulfolane, and hydrofluoric acid comprising the sequential steps of separating hydrofluoric acid from said mixture to provide an intermediate stream containing less than about 30 percent hydrofluoric acid by weight and gravitationally separating said intermediate stream into a sulfolane-enriched stream and a conjunct polymer-enriched stream. The method finds particular utility in regenerating an HF/sulfolane catalyst separating conjunct polymers from an HF/sulfolane catalyst used in an isoparaffin-olefin alkylation process. The hydrofluoric acid concentration of the mixture is preferably decreased by stripping. While any suitable inert stripping fluid may be employed, an isoparaffin is preferred, and an isoparaffin suitable for isoparaffin-olefin alkylation such as isobutane is still more preferred. Two sequential stripping steps may be used, as the sulfolane/conjunct polymer phases appear to separate more readily as the hydrofluoric acid concentration is decreased. If two-stage stripping is used, a second insert stripping fluid such as nitrogen is preferred.

The surprising effects of sequentially stripping hydrofluoric acid from the mixture before gravitational separation become evident when the mixture is stripped to hydrofluoric acid levels of less than about 30 weight percent. Separation improves as the hydrofluoric acid content is decreased, with intermediate stream hydrofluoric acid concentrations preferably falling below 25 percent by weight, more preferably below about 10 percent hydrofluoric acid by weight, and most preferably below about 5 percent by weight.

COMPARATIVE EXAMPLE

A mixture of hydrofluoric acid, sulfolane, and conjunct polymeric byproducts (which conjunct polymeric byproducts are evolved from the catalytic alkylation of isobutane with butene, referred to hereinafter as acid soluble oil or ASO) containing about 65 weight percent hydrofluoric acid, 30 weight percent sulfolane and about 5 weight percent ASO, is charged to a decantation vessel at ambient temperature and pressure sufficient to maintain the mixture in the liquid phase. The mixture is allowed to stand for approximately 24 hours. No phase separation is observed.

EXPERIMENTAL EXAMPLE 1

A mixture of hydrofluoric acid, sulfolane, and (having the same composition as the mixture of the Comparative Example, above) is charged to a stripping tower having three stages. Isobutane is introduced into the tower at a level below the height of the liquid (HF/sulfolane/ASO) charge point, and the isobutane and mixture charge rates are to maximize stripping of HF while operating below the flooding point of the tower. A stripped liquid is withdrawn from the bottom of the tower and a HF-enriched isobutane stream is withdrawn from the top of the tower. The stripped liquid contains less than about 30 percent by weight of hydrofluoric acid.

The stripped liquid is then charged to a decantation vessel and allowed to stand for approximately 24 hours. The mixture separates into two distinct phases, an upper, less dense ASO-enriched phase, and a lower, more dense, sulfolane-enriched phase.

EXPERIMENTAL EXAMPLES 2-4

Additional samples of the mixture of hydrofluoric acid, sulfolane, and ASO (having the same composition as the mixture of the Comparative Example) are stripped with isobutane to hydrofluoric acid contents of 25 weight percent, 10 weight percent, and 5 weight percent, respectively. The stripped mixtures containing lower concentrations of hydrofluoric acid are found to be separate into two distinct phases more rapidly than the stripped mixture containing 30 weight percent hydrofluoric acid.

EXPERIMENTAL EXAMPLE 5

The HF/sulfolane sample of Example 5 has the following composition:

| | |
|---|---|
| HF | 62 wt. % |
| Sulfolane | 27 wt. % |
| Isobutane | 4 wt. % |
| Water | 1-2 wt. % |
| ASO | 3 wt. % |
| Balance to 100% other hydrocarbons. | |

This mixture is a single liquid phase at 90° F. and 120 psig.

The sample is brought to atmospheric pressure and room temperature and ost of the light hydrocarbons and part of the HF are vented off. Under these conditions, the sample is a single liquid phase containing about 50 wt. % HF.

Nitrogen is then bubbled through the mixture at room temperature and atmospheric pressure to strip HF off the mixture. As the mixture is depleted in HF, the mixture separates into two phases. In Example 5, the two phases appear within several minutes of the HF concentration reaching about 2 wt. %.

Both phases are analyzed, and the dense phase (specific gravity about 1.26) contains 83.2 wt. % sulfolane, 2.2 wt. % ASO, and the balance water, salts, and a sludge. The lighter phase, having a density of less than about 1, contains 82.8 wt. % ASO, 13.3 wt. % sulfolane, and the balance of salts.

Changes and modifications in the specifically described embodiments can be carried out without departing from the scope of the invention which is intended to be limited only by the scope of the appended claims.

What is claimed is:

1. A method for separating conjunct polymers and sulfolane from a mixture containing conjunct polymers, sulfolane, and hydrofluoric acid comprising the sequential steps of separating hydrofluoric acid from said mixture to provide an intermediate stream containing less than about 30 percent hydrofluoric acid by weight and gravitationally separating said intermediate stream into a sulfolane-enriched stream and a conjunct polymer-enriched stream.

2. The method of claim 1 wherein said conjunct polymers are formed as byproduct in an isoparaffin-olefin alkylation process.

3. The method of claim 1 wherein said hydrofluoric acid is separated from s id mixture by stripping.

4. The method of claim 3 wherein said stripping fluid comprises an isoparaffin.

5. The method of claim 3 wherein said stripping step comprises sequentially stripping said mixture with isoparaffin and then stripping said mixture with nitrogen.

6. The method of claim 1 wherein said hydrofluoric acid separation step provides an intermediate stream containing less than about 25 percent hydrofluoric acid by weight.

7. The method of claim 6 wherein said hydrofluoric acid separation step provides an intermediate stream containing less than about 10 percent hydrofluoric acid by weight.

8. The method of claim 7, wherein said hydrofluoric acid separation step provides an intermediate stream containing less than about 5 percent hydrofluoric acid by weight.

* * * * *